(12) United States Patent
Paalasmaa et al.

(10) Patent No.: US 11,298,075 B2
(45) Date of Patent: Apr. 12, 2022

(54) PHYSIOLOGICAL MONITORING METHOD AND SYSTEM

(71) Applicant: Apple Inc., Cupertino, CA (US)

(72) Inventors: Joonas Paalasmaa, Helsinki (FI); Lasse Leppäkorpi, Kirkkonummi (FI); Juhani Palttala, Espoo (FI)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 14/133,694

(22) Filed: Dec. 19, 2013

(65) Prior Publication Data

US 2015/0173671 A1 Jun. 25, 2015

(51) Int. Cl.
*A61B 5/00* (2006.01)
*A61B 5/11* (2006.01)
(Continued)

(52) U.S. Cl.
CPC .......... *A61B 5/4815* (2013.01); *A61B 5/0022* (2013.01); *A61B 5/0205* (2013.01); *A61B 5/11* (2013.01); *A61B 5/1115* (2013.01); *A61B 5/1118* (2013.01); *A61B 5/4806* (2013.01); *A61B 5/6891* (2013.01); *A61B 5/7282* (2013.01); *A61B 5/024* (2013.01); *A61B 5/05* (2013.01); *A61B 5/08* (2013.01);
(Continued)

(58) Field of Classification Search
CPC ....... A61B 5/4815; A61B 5/0022; A61B 5/11; A61B 2562/0204; A61B 5/1115; A61B 5/1118; A61B 5/4806; A61B 5/6891; A61B 5/7282; A61B 5/024; A61B 5/05; A61B 5/08; A61B 5/0816; A61B 5/113; A61B 5/7246
See application file for complete search history.

(56) References Cited

U.S. PATENT DOCUMENTS

| 5,483,261 A | 1/1996 | Yasutake |
| 5,488,204 A | 1/1996 | Mead et al. |

(Continued)

FOREIGN PATENT DOCUMENTS

| JP | 2000-163031 A | 6/2000 |
| JP | 2002-342033 A | 11/2002 |

(Continued)

OTHER PUBLICATIONS

International Search Report and Written Opinion of the International Searching Authority; PCT/FI2014/051026; dated Apr. 22, 2015 (5 pages).

(Continued)

*Primary Examiner* — Lynsey C Eiseman
*Assistant Examiner* — Amanda L Steinberg
(74) *Attorney, Agent, or Firm* — Brownstein Hyatt Farber Schreck, LLP

(57) ABSTRACT

A method and system of physiological monitoring, includes measuring a quantity relating to a first subject with a first sensor positioned in or in proximity of the first subject and configured to provide a first signal, measuring a quantity relating to a second subject with a second sensor positioned in or in proximity of the second subject and configured to provide a second signal, and analyzing the first and the second signal and the interrelation of the first and second signal in order to determine at least one event relating to the first and/or the second subject.

16 Claims, 4 Drawing Sheets

(51) Int. Cl.

| | |
|---|---|
| *A61B 5/0205* | (2006.01) |
| *A61B 5/08* | (2006.01) |
| *A61B 5/113* | (2006.01) |
| *A61B 5/05* | (2021.01) |
| *A61B 5/024* | (2006.01) |

(52) U.S. Cl.
CPC ............ *A61B 5/0816* (2013.01); *A61B 5/113* (2013.01); *A61B 5/7246* (2013.01); *A61B 2562/0204* (2013.01)

(56) References Cited

U.S. PATENT DOCUMENTS

| | | | |
|---|---|---|---|
| 5,825,352 | A | 10/1998 | Bisset et al. |
| 5,835,079 | A | 11/1998 | Shieh |
| 5,880,411 | A | 3/1999 | Gillespie et al. |
| 6,188,391 | B1 | 2/2001 | Seely et al. |
| 6,310,610 | B1 | 10/2001 | Beaton et al. |
| 6,323,846 | B1 | 11/2001 | Westerman et al. |
| 6,690,387 | B2 | 2/2004 | Zimmerman et al. |
| 7,015,894 | B2 | 3/2006 | Morohoshi |
| 7,184,064 | B2 | 2/2007 | Zimmerman et al. |
| 7,663,607 | B2 | 2/2010 | Hotelling et al. |
| 7,726,209 | B2 | 6/2010 | Ruotoistenmaki |
| 8,348,840 | B2 * | 1/2013 | Heit ............... A61M 21/00 600/300 |
| 8,398,538 | B2 | 3/2013 | Dothie et al. |
| 8,479,122 | B2 | 7/2013 | Hotelling et al. |
| 8,548,770 | B2 | 10/2013 | Yuen et al. |
| 2005/0143617 | A1 * | 6/2005 | Auphan ............... A61B 5/08 600/26 |
| 2006/0197753 | A1 | 9/2006 | Hotelling |
| 2007/0008154 | A1 * | 1/2007 | Albert ............... G08B 17/00 340/573.1 |
| 2008/0009685 | A1 * | 1/2008 | Kim ............... A61B 5/4815 600/300 |
| 2008/0052837 | A1 | 3/2008 | Blumberg |
| 2008/0306396 | A1 | 12/2008 | Ariav et al. |
| 2008/0308112 | A1 * | 12/2008 | Aarts ............... A61F 5/56 128/848 |
| 2009/0121826 | A1 * | 5/2009 | Song ............... A61B 5/11 340/3.1 |
| 2010/0094139 | A1 | 4/2010 | Brauers et al. |
| 2010/0099954 | A1 | 4/2010 | Dickinson et al. |
| 2010/0217618 | A1 * | 8/2010 | Piccirillo ............. G06F 19/327 705/2 |
| 2010/0283618 | A1 * | 11/2010 | Wolfe ............... A61B 7/003 340/575 |
| 2010/0305481 | A1 | 12/2010 | Igney |
| 2011/0015495 | A1 | 1/2011 | Dothie et al. |
| 2011/0190594 | A1 * | 8/2011 | Heit ............... A61M 21/00 600/301 |
| 2011/0224510 | A1 * | 9/2011 | Oakhill ............... A61B 5/11 600/301 |
| 2011/0295083 | A1 * | 12/2011 | Doelling ............... A61B 5/103 600/301 |
| 2012/0138067 | A1 * | 6/2012 | Rawls-Meehan .... A47C 20/041 128/845 |
| 2012/0179066 | A1 * | 7/2012 | Hsu ............... G06F 19/3418 600/586 |
| 2013/0046151 | A1 * | 2/2013 | Bsoul ............... A61B 5/4806 600/301 |
| 2013/0174345 | A1 * | 7/2013 | Leu ............... A47C 21/00 5/694 |
| 2013/0245465 | A1 * | 9/2013 | Kasama ............... A61B 5/4812 600/483 |
| 2013/0261404 | A1 * | 10/2013 | Sato ............... A61B 5/4806 600/300 |
| 2013/0267791 | A1 * | 10/2013 | Halperin ............... A61B 5/6892 600/300 |
| 2013/0310657 | A1 | 11/2013 | Sullivan |
| 2014/0276227 | A1 * | 9/2014 | Perez ............... A61B 5/4818 600/586 |
| 2014/0371635 | A1 * | 12/2014 | Shinar ............... A61B 5/6891 600/595 |

FOREIGN PATENT DOCUMENTS

| | | |
|---|---|---|
| JP | 2006014765 A | 1/2006 |
| JP | 2007327993 A | 12/2007 |
| WO | 2007143535 A3 | 8/2008 |
| WO | 2010070463 A1 | 6/2010 |
| WO | 2011140113 A1 | 11/2011 |
| WO | 2013/030428 A1 | 3/2013 |

OTHER PUBLICATIONS

Dittami, J. et al. (Oct. 1, 2007). "Sex Differences in the Reactions to Sleeping in Pairs Versus Sleeping Alone in Humans," Sleep and Biological Rhythm, 5(4): 271-276.

Lee, S.K. et al. (Apr. 1985). "A Multi-Touch Three Dimensional Touch-Sensitive Tablet," *Proceedings of CHI: ACM Conference on Human Factors in Computing Systems*, pp. 21-25.

Rubine, D.H. (Dec. 1991). "The Automatic Recognition of Gestures," CMU-CS-91-202, Submitted in Partial Fulfillment of the Requirements for the Degree of Doctor of Philosophy in Computer Science at Carnegie Mellon University, 285 pages.

Rubine, D.H. (May 1992). "Combining Gestures and Direct Manipulation," CHI '92, pp. 659-660.

Westerman, W. (Spring 1999). "Hand Tracking, Finger Identification, and Chordic Manipulation on a Multi-Touch Surface," A Dissertation Submitted to the Faculty of the University of Delaware in Partial Fulfillment of the Requirements for the Degree of Doctor of Philosophy in Electrical Engineering, 364 pages.

* cited by examiner

PHYSIOLOGICAL MONITORING METHOD AND SYSTEM

TECHNICAL FIELD

The aspects of the present disclosure generally relate to physiological monitoring. In particular, but not exclusively, the aspects of the present disclosure relate to simultaneous physiological monitoring of two subjects. In particular, but not exclusively, the aspects of the present disclosure generally relate to sleep monitoring. In particular, but not exclusively, the aspects of the present disclosure relate to sleep monitoring in a double bed.

BACKGROUND ART

Physiological monitoring is carried out with devices that don't require measuring electrocardiography, electroencephalography or other electrophysiological signals with uncomfortable electrodes, but are based on comfortable movement and audio measurement. The measurements needed for such unobtrusive monitoring are carried out using systems such as microphones for measuring movement sounds, breathing sounds and snoring; movement sensors such as radars, bed-installed force sensors, wearable movement sensors and further sensors for measuring movements, respiration and heart rate.

Unobtrusive monitoring systems are known e.g. from documents WO2007143535, U.S. Pat. No. 8,398,538, WO2011140113, U.S. Pat. Nos. 8,548,770 and 7,726,209.

When monitoring physiological parameters, e.g. the sleep of a single person sleeping in a bed, practically all measurement data from the unobtrusive sensors relate to the sleeping person, obviously with expected external influences, such as ambient noise, disturbing the measurement. However, when physiological parameters of two or more people are to be monitored, e.g. two people are sleeping in a same bed, unobtrusive monitoring becomes more difficult.

In a typical measurement scenario each person being monitored would have their own unobtrusive sensor. The output of each sensor will inexorably contain information also on the person who is not meant to be monitored with the sensor in question, i.e. for example a movement sensor of a first person will also detect movements of a second person and vice versa. The magnitude of the problem depends on the unobtrusive sensor employed, e.g. microphones are more prone to pick up signals from several persons.

It would be advantageous to mitigate the problems related to multi-person physiological monitoring with unobtrusive measurements.

SUMMARY

According to a first example aspect of the present disclosure there is provided a method of physiological monitoring, comprising measuring a quantity relating to a first subject with a first sensor positioned in or in proximity of the first subject and configured to provide a first signal;

measuring a quantity relating to a second subject with a second sensor positioned in or in proximity of the second subject and configured to provide a second signal; and analyzing the first and the second signal and the interrelation of the first and second signal in order to determine at least one event relating to the first and/or the second subject.

The first and the second subject may be in a bed and the first and the second sensor may be positioned in or in proximity of the bed.

The first and the second sensor may be configured to measure a same quantity relating to the subject.

The quantity may be heart rate.

The quantity may be respiration.

The quantity may be related to movement.

The quantity may be audio signal.

The event may be the presence of the subject.

The event may be movement of the subject.

The event may sounds made by the subject.

Prior to analysis the signals may be transmitted to a control unit.

The signals may be transmitted independently with added information on the association of the signals to the subjects.

The signals may be transmitted together.

The first and second sensors may be unobtrusive sensors.

The first and the second sensor may comprise force sensors.

The method may further comprise measuring a quantity relating to the first and/or second subject with a third sensor and/or fourth sensor positioned in or in proximity of the first and/or the second subject and configured to provide a third and/or fourth signal.

The method may further comprise analyzing the first, the second, the third and/or the fourth signal and their interrelation in order to determine at least one event relating to the first and/or the second subject.

The third and/or fourth sensor may comprise audio sensors.

The method may further comprise providing a sleep quality determination based on the analysis.

According to a second example aspect of the present disclosure there is provided a physiological monitoring system, comprising a first sensor positioned in or in proximity of a first subject and configured to measure a quantity relating to the first subject and to provide a first signal;

a second sensor positioned in or in proximity of a second subject and configured to measure a quantity relating to a second subject and to provide a second signal; and a control unit configured to analyze the first and the second signal and the interrelation of the first and second signal in order to determine at least one event relating to the first and/or the second subject.

The first and the second sensor may be configured to measure a same quantity relating to the subject.

The quantity may be heart rate.

The quantity may be respiration.

The quantity may be related to movement.

The quantity may be audio.

The event may be the presence of the subject.

The event may be movement of the subject.

The event may be sounds made by the subject.

The sensors may be configured to transmit the signals to the control unit prior to the analysis.

The sensors may be configured to transmit the signals independently with added information on the association of the signals to the subjects.

The sensors may be configured to transmit the signals together.

The control unit may be positioned in proximity of the bed.

The control unit may be integrated into an electronic device.

The electronic device may comprise a smartphone.

The control unit may be implemented in a cloud service.

The control unit may be configured to provide a sleep quality determination based on the analysis.

The first and second sensors may comprise unobtrusive sensors.

The first and the second sensor may comprise force sensors.

The system may further comprise a third sensor and/or fourth sensor positioned in or in proximity of the first and/or the second subject and configured to measure a quantity relating to the first and/or second subject and to provide a third and/or fourth signal.

The control unit may further be configured to analyze the first, the second, the third and/or the fourth signal and their interrelation in order to determine at least one event relating to the first and/or the second subject.

The third and/or fourth sensor may comprise audio sensors.

According to a third example aspect of the present disclosure there is provided a computer program comprising computer code for causing performing the method of the first example aspect, when executed by an apparatus.

According to a fourth example aspect of the present disclosure there is provided a memory medium comprising the computer program of the third example aspect.

Different non-binding example aspects and embodiments of the present disclosure have been illustrated in the foregoing. The above embodiments are used merely to explain selected aspects or steps that may be utilized in implementations of the present disclosure. Some embodiments may be presented only with reference to certain example aspects of the present disclosure. It should be appreciated that corresponding embodiments may apply to other example aspects as well.

BRIEF DESCRIPTION OF THE DRAWINGS

Some example embodiments of the present disclosure will be described with reference to the accompanying drawings, in which.

DETAILED DESCRIPTION

In the following description, like reference signs denote like elements. A skilled person appreciates that although embodiments of the present disclosure have been explained with reference to sleep monitoring in a bed, the present disclosure is applicable in analogue manner to any physiological monitoring in any situation in which similar problems arise, for example the physiological parameters of persons sitting next to each other or engaged in physical activity near each other can be monitored.

Figure 1:
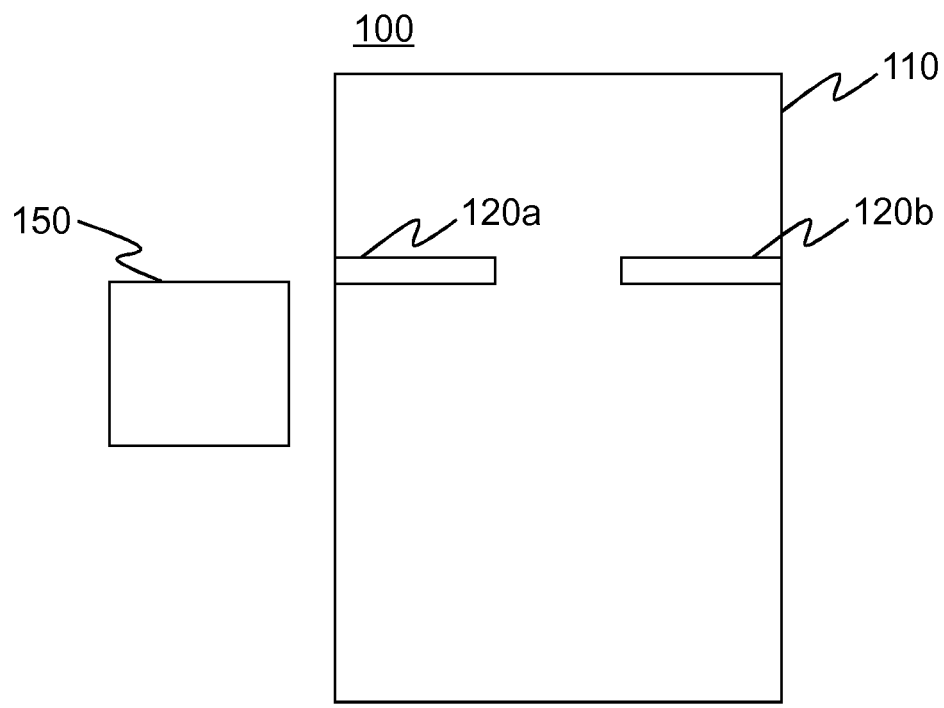
FIG. 1 shows a schematic example presentation of a system according to an embodiment of the present disclosure.

FIG. 1 shows a schematic example presentation of a system 100 according to an embodiment of the present disclosure. The system comprises a control unit 150 and at least a first and a second unobtrusive sensor 120a,120b. The sensors 120a,120b are in an embodiment positioned for example in or in proximity of a bed 110, or on the subject monitored as hereinafter described, and are configured to provide a first signal and a second signal, respectively. It should be noted that the term double bed is used hereinafter to refer to any sleeping place, such as a bed, mattress or sleeping sofa, in which several persons are able to sleep and/or lie down, and also to several separate beds in the same space and in proximity of each other. In a further example embodiment each unobtrusive sensor 120a,120b comprises several separate sensor elements forming a multi-channel sensor. In an embodiment, the unobtrusive sensors 120a,120b comprise force sensors. The force sensors are in an embodiment positioned e.g. under a bedpost, under a mattress or between a mattress and a bed sheet of a double bed 110 in order to measure for example respiration, heart rate and movement of a first and a second person in the bed, respectively.

The unobtrusive sensors 120a,120b comprise in an embodiment elongated strips comprising one or several force sensing elements. The force sensing elements comprise sensor elements such as piezoelectric, capacitive or resistive elements. A skilled person appreciates that any known force sensing element is applicable instead or in addition to the above-mentioned sensor element types. The unobtrusive sensors 120a,120b comprise in an embodiment movement sensors or accelerometers, installed in the bed or worn by the subject, and/or radars.

The control unit 150 comprises elements configured to carry out functionalities such as signal analysis, communications, storing and displaying of data. The control unit 150 comprises elements (not shown) known in processing devices, such as processors, memory units, communication circuits, I/O (input/output) units, user interface units, connectors and antennas. The control unit 150 is connected to the unobtrusive sensors either with hardware connectors or wirelessly using wireless communication such as Bluetooth, wireless local area network (WLAN) or proprietary radio communication protocols. In a further embodiment, the control unit is implemented using a remote server system, such as a cloud service or implemented as an application on an electronic device such as a smartphone, a tablet computer, a television or a table computer. In a still further embodiment, the control unit, or the functionalities thereof, are implemented into the unobtrusive sensors 120a,120b.

Figure 2:
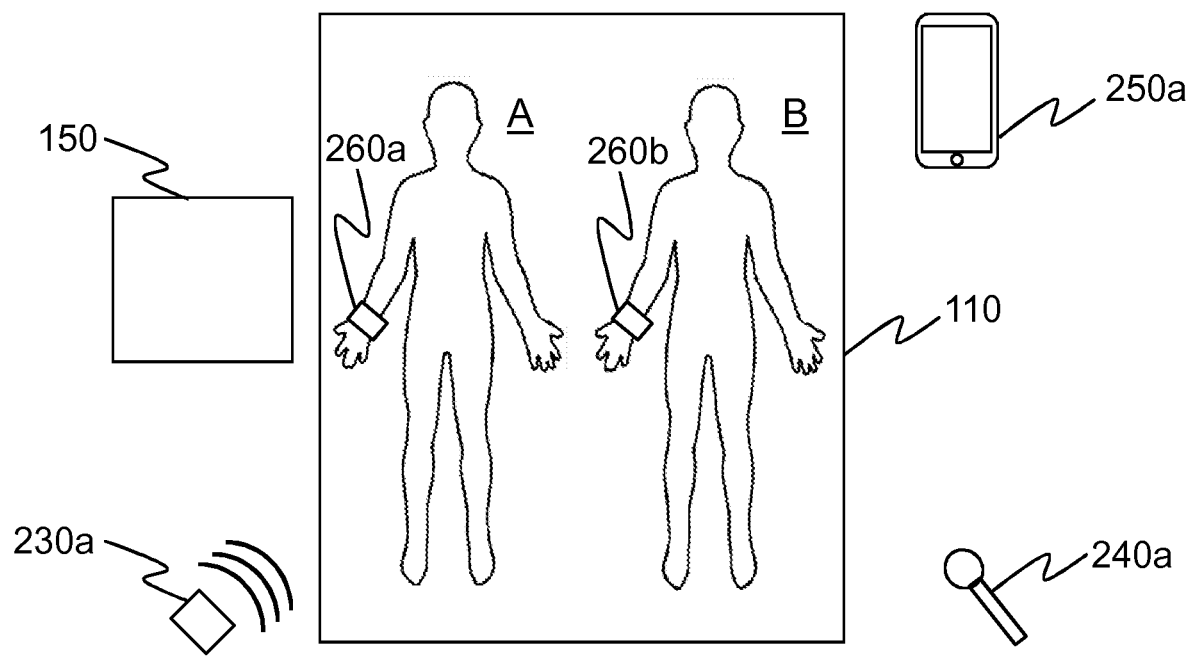
FIG. 2 shows a schematic example presentation of a system according to an embodiment of the present disclosure.

FIG. 2 shows a schematic example presentation of a system 100 according to an embodiment of the present disclosure. Again, the system comprises a control unit 150 as hereinbefore described and unobtrusive sensors. As hereinbefore previously described, the system comprises two or more unobtrusive sensors configured to monitor physiological parameters, e.g. sleep, of a person or persons, or subjects A and B. FIG. 2 shows types of unobtrusive sensors configured for sleep monitoring, such as a radar 230a, for example a doppler radar, a microphone 240a and a smartphone 250a, the sensor elements comprised in which are utilized in the system. Furthermore, the subjects A and B are shown wearing wrist actigrams 260a,260b. It is to be noted that in a further embodiment, other unobtrusive sensor types are used, for example sensors measuring a quantity relating to movement of a subject. For example in addition to or instead of wrist actigrams, systems attachable to arm, or head of a subject could be used. Furthermore, in an embodiment instead of or in addition to wrist actigrams, for example smart watches or smart glasses, or clothes with integrated electronics, i.e. smart clothing, is used. In accordance with embodiments of the present disclosure, two or more sensors of the same type or two or more sensors of different types are used, for example two force sensors and a microphone are used together.

According to the present disclosure, the respiration, heart rate, movement, and/or sounds of a person or persons for example sleeping in a bed are measured by one or more sensors. It should be noted that the person or persons need not sleep, i.e. the sensors measure the variables independent of the actual sleeping state, and are also applicable in situations other than sleeping. In case there are several persons in the bed and depending on the type of the sensors and their position, each sensor signal comprises data not only concerning a single person but also data pertinent to the other person. In accordance with the present disclosure, each person is monitored individually, despite the cross-talk between the sensors. The amount of cross-talk between the sensors, i.e. how strongly for example the heartbeat of the person sleeping on one side of the bed shows up on the sensor signal of the person sleeping on the other side, depends for example on the type of sensor used. For example audio is carried over very strongly, but e.g. on a force sensor the movements of both persons are strongly registered whereas the cross-talk in heartbeat signal depends for example on the type of mattress and sensor placement.

The sensors provide signals on a subject or on both subjects, and on several quantities relating to physiological parameters of the subjects, and to e.g. monitoring their sleep. As hereinbefore described the signals can be measured with different types of sensors. The sounds caused by the subjects or external sources are measured with an audio sensor, such as a microphone, for example integrated into an electronic device such as a smartphone. The movement and respiration of the subjects is measured with audio sensors, force sensors in or in proximity of the bed, video-based sensors, radars and/or wearable sensors as hereinbefore and hereinafter described. The heart rate of a subject is measured with force sensors, radars and/or wearable sensors as hereinbefore and hereinafter described.

In an embodiment, the respiration and/or heartbeat signals are measured on both sides of the bed, for example using elongated force sensor strips as depicted in FIG. 1. The signals from the sensors are analyzed with different methods, e.g. by comparing different characteristics of the signals. For example, the length of respiration cycles, the beginnings of the cycles or the ends of the cycles are compared between the signals. In a further embodiment, the signals are analyzed using statistical or probabilistic methods and/or methods based on information theory, such as mutual information, entropy or correlation with time delay. In an embodiment the signal analysis is carried out with a suitable algorithm implemented with software and/or hardware in the control unit 150. In an embodiment wherein the control unit is implemented in cloud based service or as an application in an electronic device, the algorithm is implemented in the same.

Figure 3:
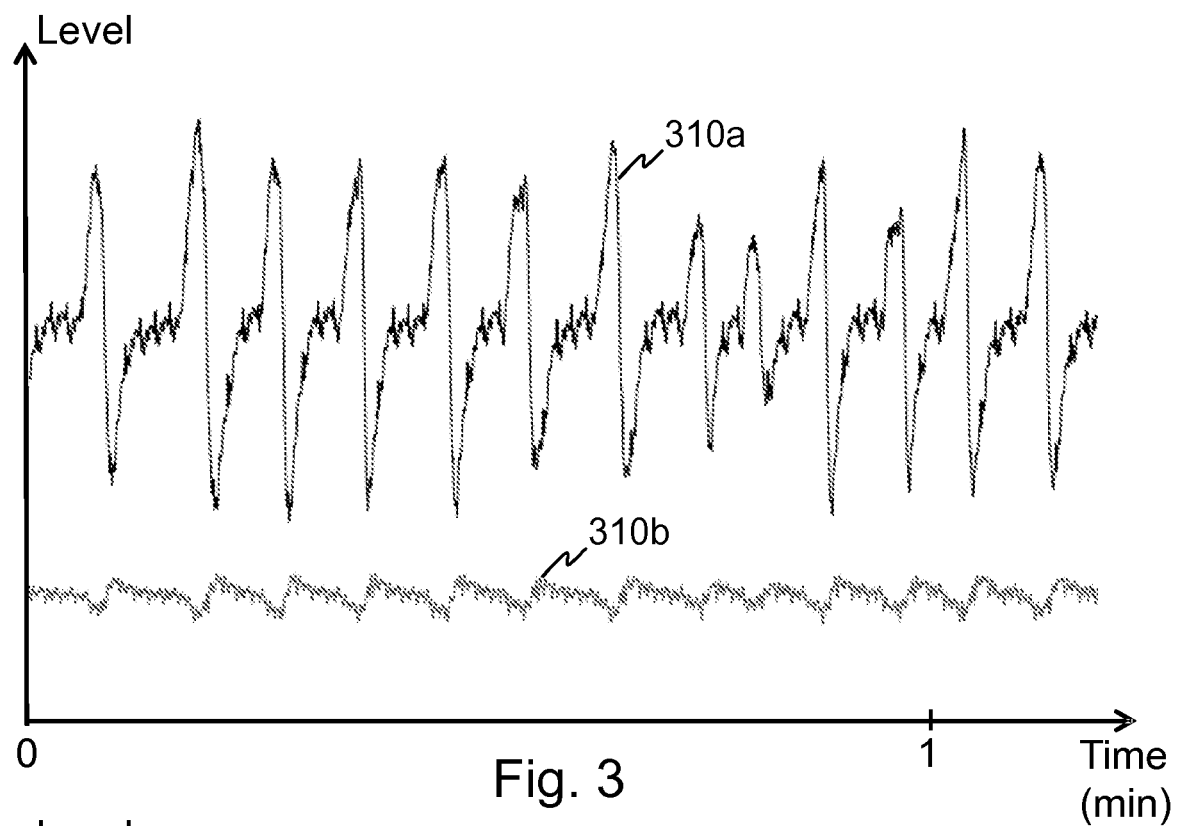
FIG. 3 shows example signals measured by a system according to the present disclosure in a situation with a single person sleeping in a bed.

Both sensors provide a signal, and the signals and their interrelations are analyzed in order to determine events relating to the subjects in bed, e.g. a state of the subjects in bed, such as present or awake, and/or actions relating to the subjects in bed, such as moving, changing sleeping posture, or making sounds. FIG. 3 shows an example of respiration/heartbeat signals 310a,310b from a first sensor and from a second sensor. The horizontal axis of the chart shows time in minutes and the vertical axis shows the level of the signal, for example the voltage or current provided by the sensor. Respiration and heartbeat events in signals 310a,310b are synchronized, which will be detected with the signal analysis, and accordingly, only a single person is present in bed. Furthermore, a comparison of the levels of the signals shows that the person on the side of the first sensor 310a, i.e. subject A, is present.

Figure 4:
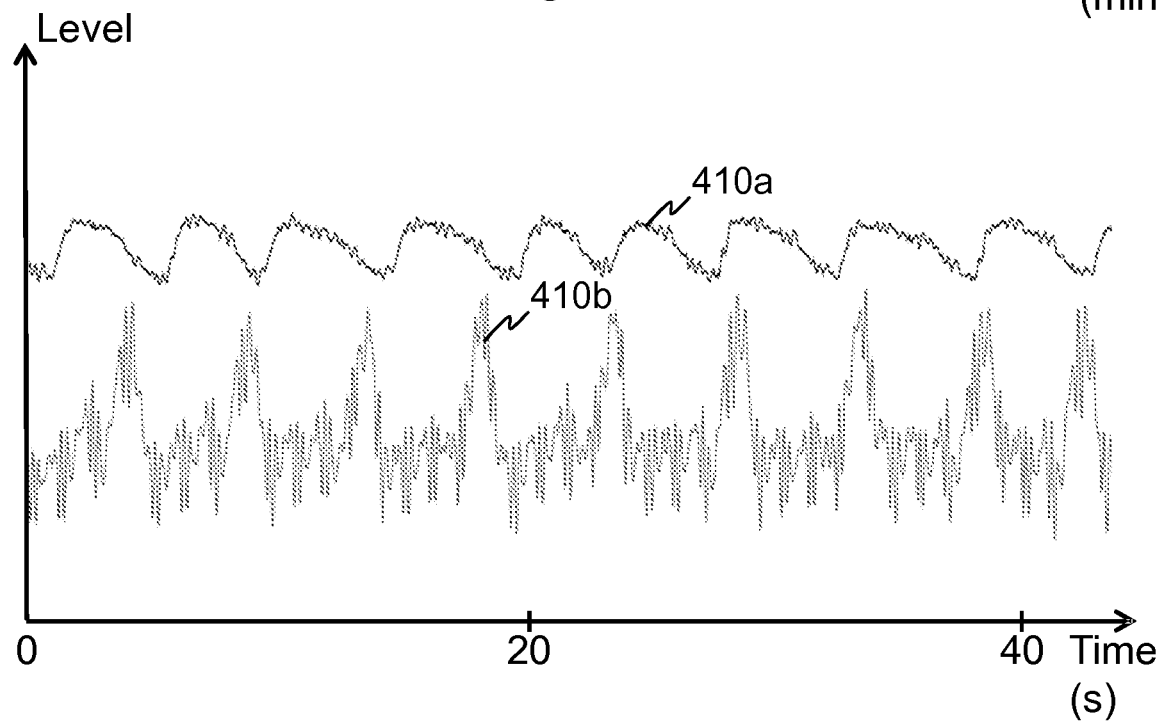
FIG. 4 shows example signals measured by a system according to the present disclosure in a situation with two persons sleeping in a bed.

FIG. 4 shows an example of respiration/heartbeat signals 410a,410b from a first sensor and from a second sensor. Again, the horizontal axis of the chart shows time in seconds and the vertical axis shows the level of the signal, for example the voltage or current provided by the sensor. Respiration and heartbeat events in signals 410a,410b are not synchronized, which will be detected with the signal analysis, and accordingly, two persons, subjects A and B, are present in bed. Furthermore, a comparison of the levels of the signals shows that levels of the signals are comparable, the signal level obviously being affected also by other factors than presence of the subject, such as the sleeping position of the subject. In an embodiment, first criteria for determining whether a person is present, is that the amplitude of the signal of the respective sensor exceeds a predetermined level, and after the first criteria has been fulfilled, the synchronization of signals is checked. Furthermore, in an embodiment, if it is determined that one of the subjects is not present, no further analysis are carried out for that subject.

In a further embodiment, the presence determination is further improved by taking into account the movements of the persons in bed, since entering or exiting the bed requires major movement that will likely show up on any sensor signal. Accordingly, the signal analysis algorithm or algorithms used may be configured to maintain the presence state of the subject until a major movement is detected, i.e. a person present in bed cannot exit the bed without a major movement being detected. In an embodiment, such constraint in the presence analysis is implemented for example by modeling the present/absent states as a hidden Markov model and constraining that the transition from present to absent and vice versa can only happen during movement.

Figure 5:
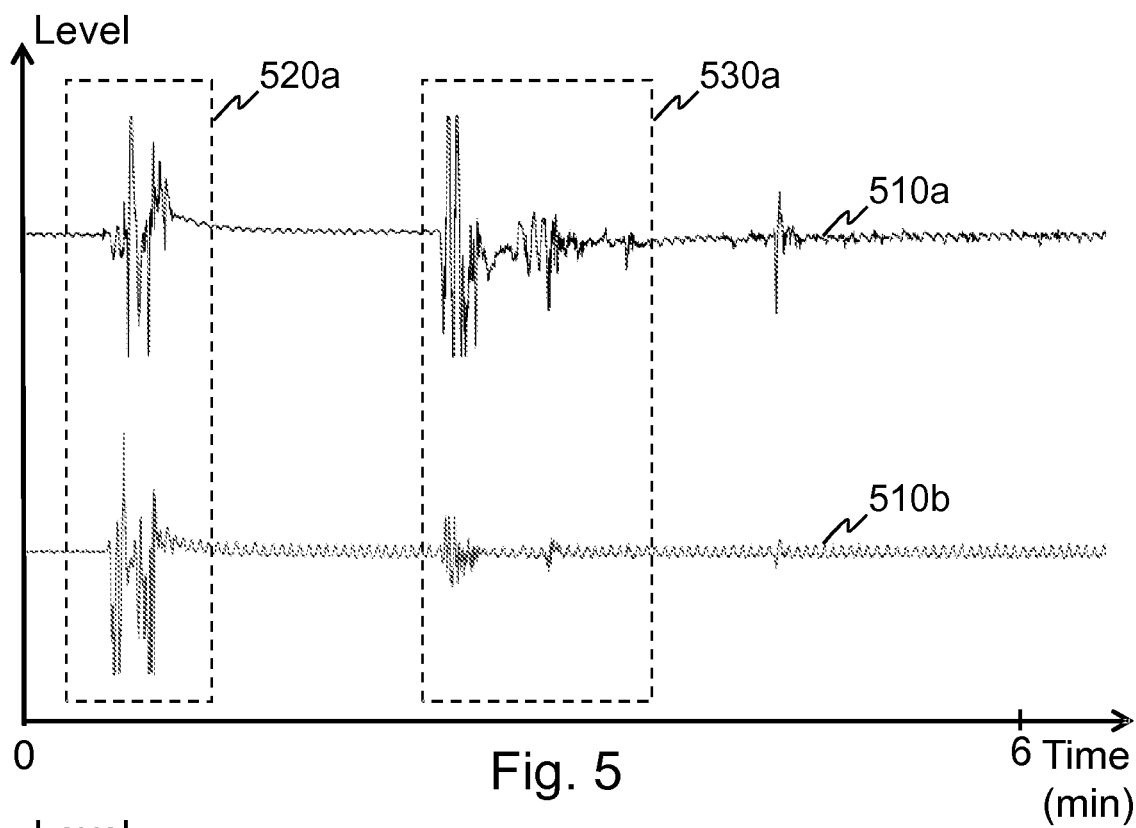
FIG. 5 shows example signals measured by a system according to the present disclosure in a situation with two persons sleeping in a bed and moving.

FIG. 5 shows an example of respiration/heartbeat signals 510a,510b from a first sensor and from a second sensor with movement being detected. Again, the horizontal axis of the chart shows time in minutes and the vertical axis shows the level of the signal, for example the voltage or current provided by the sensor. Detection of movements is an important part of sleep monitoring and analysis of quality of sleep. When more than one person is sleeping in a bed, the movement of each person shows in each sensor signal, i.e. also the sensor on the other side of the bed or meant for the other person records the movement. The magnitude of the measured movement depends on the sensor type. Sensors that have a large receptive area, such as radars, pick up strong movement signals in these situations. FIG. 5 shows a situation 520a in which both subjects move, and the movements show up with large amplitude in both signals 510a, 510b. Furthermore, FIG. 5 shows a situation 530a in which subject A makes abrupt movements which show up strongly in the signal 510a of the corresponding sensor. The movements of subject A also show up in the signal 510*b* of the other sensor. As the signals are analyzed, it is inferred that the subject, in the signal of which the movement shows up with a larger magnitude or amplitude has moved, especially if the signal morphology of the movement is similar in both sensors. Furthermore, if both signals show a similar amplitude and/or greatly differing signal morphologies, both subjects are deemed to have moved as in the beginning of the signal sequence of FIG. 5. In a further embodiment, depending on the properties of the bed and the sensors, the movement of subject B will show up in the signal of subject A with a small delay, which can further be used to refine the analysis.

In a further embodiment, the movement analysis is refined by assessing the pre- and post-movement sleeping posture of the subjects by analyzing the sensor signals recorded prior to and after the detected movement. In a further embodiment, a multi-channel sensor is used in order to more precisely determine the movements and the sleep characteristics thereinbefore and thereinafter. In a still further improvement, the movement signals are analyzed in order to determine the disturbance caused to subject A by subject B moving, by analyzing movements of subject A subsequent to the detection of subject B having moved. Similarly, it is possible to determine the significance of one of the two sleeping persons leaving the bed to the sleep quality of the remaining person.

Figure 6:
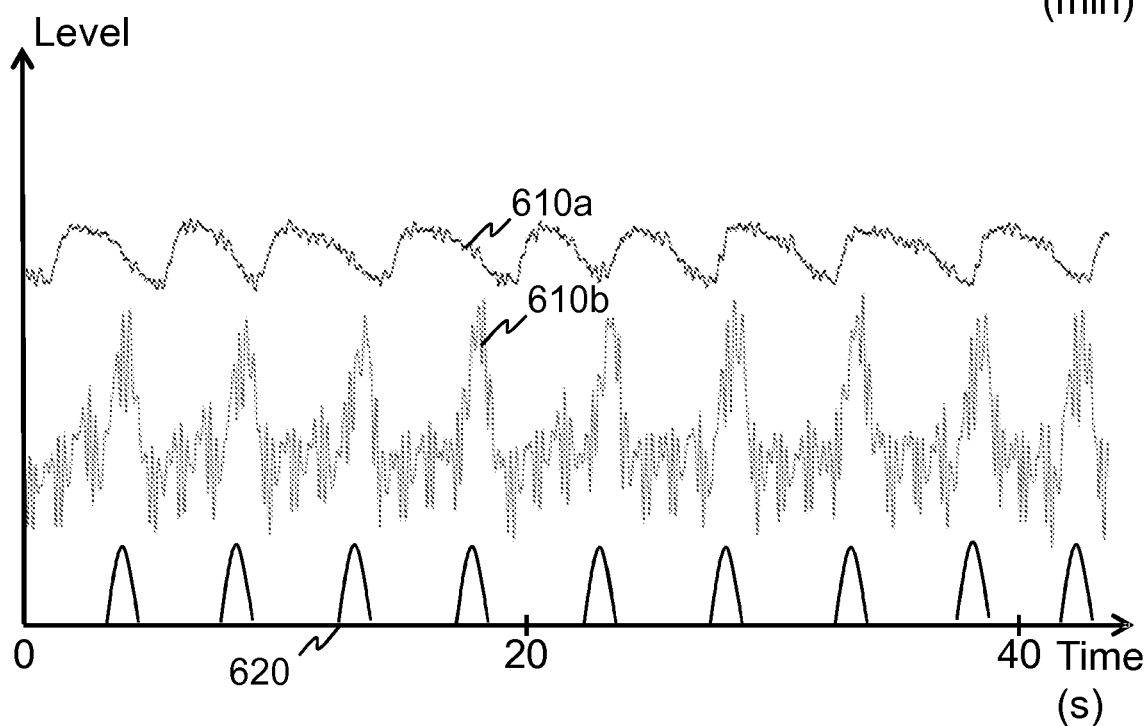
FIG. 6 shows example signals measured by a system according to the present disclosure in a situation with two persons sleeping in a bed and one of them snoring.

As hereinbefore described, several types of sensors are in an embodiment used simultaneously. In an embodiment, an audio sensor such as a microphone is used to measure sounds of the sleeping person or persons. In an embodiment for example mobile phone(s) of the person or persons sleeping is used as an audio sensor. FIG. 6 shows an example of respiration/heartbeat signals 610*a*,610*b* from a first sensor and from a second sensor with a third signal 620 from a third sensor that is an audio sensor. Again, the horizontal axis of the chart shows time in seconds and the vertical axis shows the level of the signal, for example the voltage or current provided by the sensor. The signal 620 shows a periodic detection corresponding to snoring of one of the subjects in bed. When both the subject A and subject B are present in bed, it is important for sleep monitoring to recognize which subject is snoring.

In FIG. 6 it is determined that subject B is snoring as signal analysis reveals that the signal from the audio sensor is synchronized with the respiration signal 610*b*. In a further embodiment, a more complicated signal analysis is used to determine the snoring of both subjects, as in such a case the signal 620 from the audio sensor will be in some way synchronized with both signals 610*a*,610*b*. If the signal 620 from the audio sensor is independent from both signals 610*a*,610*b* an external source is causing the sounds. In an embodiment with several audio sensors, the signal levels of both are compared in analogous manner to that described hereinbefore with respect to movement and presence. In a further embodiment, the recorded audio signal is compared with other signals in order to define the disturbances caused to the sleep of the subjects. For example, a movement recorded subsequent to noise may indicate that the sleep of the subject moving was disturbed and the quality of sleep reduced. In a further embodiment, one breathing sound signal and the respiration signal of subject A are measured, and based on the synchronization of the audio and respiration signals it is determined whether subject A snores.

Figure 7:
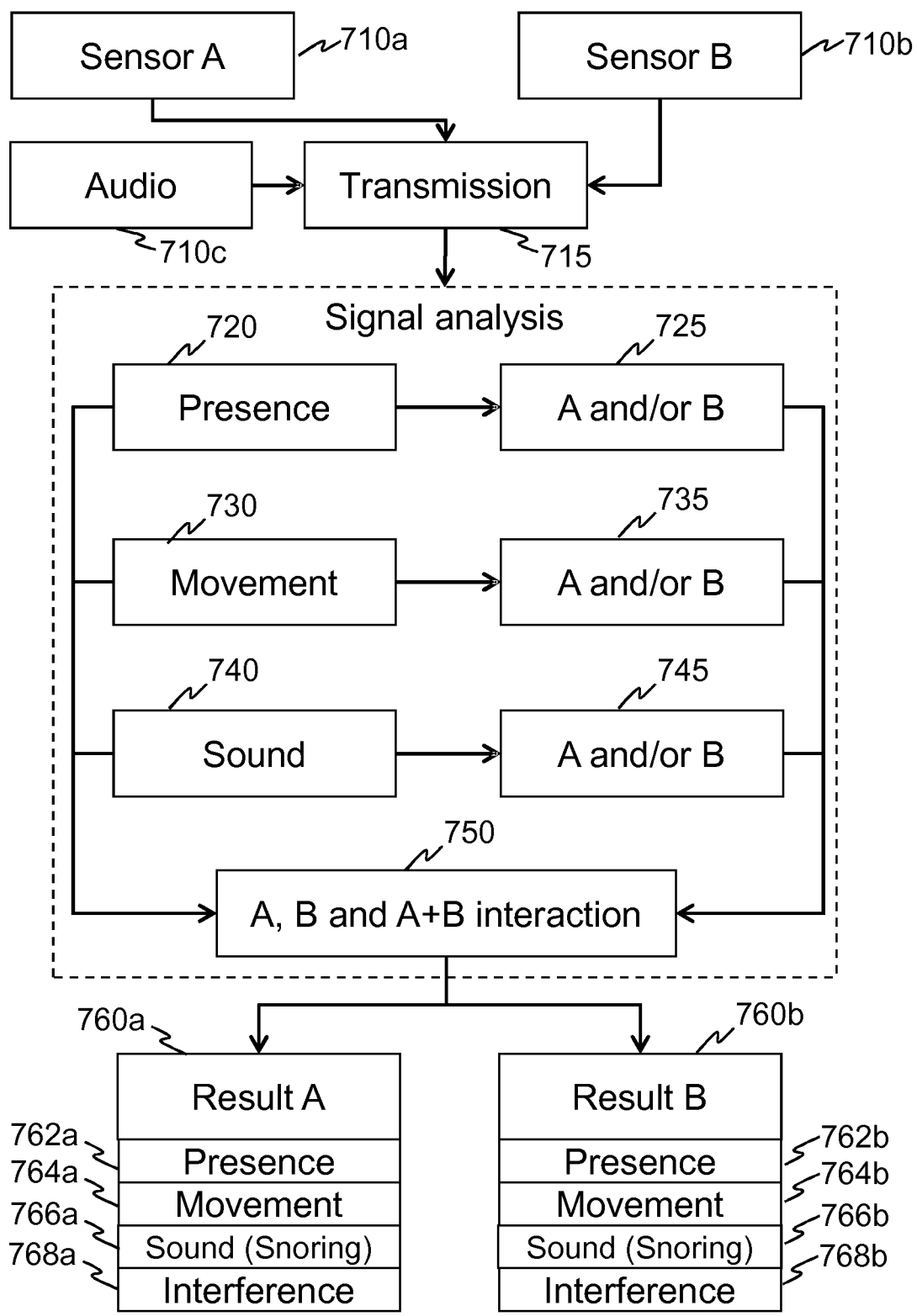
FIG. 7 shows an example flow diagram of a method according to an embodiment of the present disclosure.

FIG. 7 shows an example flow diagram of a method according to an embodiment of the present disclosure. At step 710*a*,710*b* the sensors A and B measure a quantity related to a sleeping person, such as respiration and heart rate as hereinbefore described. Furthermore, in an embodiment, an audio signal is also recorded as hereinbefore described at 710*c*. The sensors A and B provide signals comprising respiration, heart rate and movement information on subjects A and B. The respiration and heart rate in each signal mainly relates to subject A or B respectively, i.e. the carryover is not significant. However, the movement of a subject shows up on both signals. The audio signal comprises the sounds of both subjects and of external sources.

At 715 the signals from the sensors are processed and transmitted. In an example embodiment the signals are transmitted locally to a locally positioned control unit and analyzed therein. In such a case, after analysis the signals and/or results of the analysis are in an embodiment sent for example to a web service accessible with a personal computer or a mobile application. In a further embodiment, the signals are transmitted independently to a control unit implemented as a cloud service or as a mobile application. In such a case the origin of the signals, i.e. that the signals are associated to the same bed and to each other is identified for example with a location tag inserted into the signal. In a further embodiment, the locally positioned control unit, such as an electronic device, e.g. a smartphone, comprises a user interface through which the signals and the results of the signal analysis is accessible.

Subsequent to signal transmission, the signals are analyzed as hereinbefore described. The presence of the subjects in bed is analyzed at 720 in order to determine whether subjects A and/or B are present at 725. The movement of the subjects is analyzed at 730 in order to determine the movements of the subjects and their interrelations at 735. The audio signals are analyzed at 740 in order to determine whether subjects A and/or B are causing sounds, and the effect of the sounds on the other subject at 745. The analysis 720-745 are carried out concurrently and interlaced, in such a way that the results of an analysis step are in an embodiment used in further analysis in addition to or instead of the raw sensor signals.

At 750, the results of the signal analysis are combined to form a sleep monitoring analysis as to sleep quality of the subjects. The sleep monitoring analysis includes an analysis of the interaction of subjects A and B, if any. The result is shown and stored independently for subjects A and B at 760*a*,760*b* for example in a web service or application accessible to the subjects. In an example embodiment, the results for each subject contains information 762*a*-768*a*, 762*b*-768*b* on the presence, movements, snoring, and interference or disturbances caused by the other subject moving or making sounds. A skilled person appreciates that further analysis are in an embodiment carried out, and further measurement data if available is used in such further analysis. For example the type of movements may be analyzed or the sleep quality may be scrutinized further, especially if electroencephalography or electrocardiography data is available, in order to find micro-arousals and cardiac arousals.

The foregoing description has provided by way of non-limiting examples of particular implementations and embodiments of the present disclosure a full and informative description of the best mode presently contemplated by the inventors for carrying out the present disclosure. It is however clear to a person skilled in the art that the present disclosure is not restricted to details of the embodiments presented above, but that it can be implemented in other embodiments using equivalent means or in different combinations of embodiments without deviating from the characteristics of the present disclosure.

Furthermore, some of the features of the above-disclosed embodiments of this present disclosure may be used to advantage without the corresponding use of other features. As such, the foregoing description shall be considered as merely illustrative of the principles of the present present disclosure, and not in limitation thereof. Hence, the scope of the present disclosure is only restricted by the appended claims.

The invention claimed is:

1. A method of sleep monitoring, comprising:
   monitoring, using a first sensor positioned closer to a first subject than a second subject, a first sleep parameter relating to the first subject, the first sensor configured to output a first signal, the first signal at least partially based on the first sleep parameter;
   monitoring, using a second sensor positioned closer to the second subject than the first subject, a second sleep parameter relating to the second subject, the second sensor configured to output a second signal, the second signal at least partially based on the second sleep parameter;
   identifying a movement event in the first signal;
   identifying the movement event in the second signal;
   comparing, by a control unit, the first signal to the second signal, wherein comparing the first signal to the second signal comprises:
      determining a first signal amplitude associated with the movement event in the first signal and a second signal amplitude associated with the movement event in the second signal;
      comparing the first signal amplitude to the second signal amplitude, and determining a time delay between the movement event detected by the first sensor and the movement event detected by the second sensor; and
      based at least partially on comparing the first signal amplitude to the second signal amplitude, and determining the time delay between the movement event detected by the first sensor and the movement event detected by the second sensor, assigning the movement event to a movement of one of the first or second subjects.

2. The method of claim 1, wherein:
   the movement event is a first event; and
   the method further comprises:
      detecting, using the second sensor, a third signal occurring after the movement event;
      associating the third signal with a second event assigned to the second subject;
      comparing the first event and the second event; and
      determining that the second event was a result of a disturbance caused by the first event.

3. The method of claim 2, wherein the operation of determining that the second event was the result of the disturbance caused by the first event is based at least in part on an elapsed time between the first event and the second event.

4. The method of claim 1, further comprising determining a sleep quality of the first subject based, at least in part, on the first signal.

5. The method of claim 1, wherein:
   the first sleep parameter comprises at least one of a heart rate, a respiration, a movement, or sound of the first subject; and
   the second sleep parameter comprises at least one of a heart rate, a respiration, a movement, or sound of the second subject.

6. The method of claim 1, further comprising:
   monitoring, using a third sensor, a third sleep parameter relating to the first subject, the third sensor configured to output a third signal based, at least in part on, the third sleep parameter;
   comparing the first signal and the third signal; and
   determining whether the first sleep parameter and the third sleep parameter are synchronized based at least in part on the comparing.

7. The method of claim 6, wherein:
   the first sleep parameter comprises one of a heart rate, a respiration, a movement or sound of the first subject; and
   the third sleep parameter comprises one of a heart rate, a respiration, a movement or sound of the first subject; and
   the first sleep parameter is a different type of parameter than the second sleep parameter.

8. The method of claim 1, wherein:
   the first sleep parameter comprises a heart rate, a respiration, a movement, or sound of the first subject; and
   the second sleep parameter comprises a heart rate, a respiration, a movement, or sound of the second subject.

9. The method of claim 8, wherein the first and second sleep parameters are the same.

10. The method of claim 8, wherein the first and second sleep parameters are different.

11. A system for monitoring sleep, comprising:
   a first sensor positioned at a first location on or in a bed and proximate to a first subject, the first sensor configured to:
      monitor a first sleep parameter relating to the first subject; and
      output a first signal, the first signal at least partially based on the first sleep parameter;
   a second sensor positioned at a second location on the bed and proximate to a second subject, the second sensor configured to:
      monitor a second sleep parameter relating to the second subject; and
      output a second signal, the second signal at least partially based on the second sleep parameter; and
   a control unit operably connected to the first and second sensors, and configured to:
      identify a movement event in the first signal;
      identify the movement event in the second signal;
      compare the first signal to the second signal by:
         determining a first signal amplitude associated with the event in the first signal and a second signal amplitude associated with the event in the second signal;
         comparing the first signal amplitude to the second signal amplitude, and determining a time delay between the movement event detected by the first sensor and the movement event detected by the second sensor; and
         based at least partially on comparing the first signal amplitude to the second signal amplitude, and determining the time delay between the movement event detected by the first sensor and the movement event detected by the second sensor, assigning the event to a movement of one of the first or second subjects.

12. The system of claim 11, wherein:
the movement event is a first event; and
the control unit is further configured to:
  detect, using the second sensor, a third signal occurring after the movement event;
  associate the third signal with a second event assigned to the second subject;
  compare the first event and the second event; and
  determine that the second event was a result of a disturbance caused by the first event.

13. The system of claim 12, wherein the control unit is configured to determine that the second event was the result of the disturbance caused by the first event based, at least in part, on an elapsed time between the first event and the second event.

14. The system of claim 11, wherein:
the first sensor is configured to monitor at least one of a heart rate, a respiration, a movement, or sound of the first subject; and
the second sensor is configured to monitor at least one of a heart rate, a respiration, a movement, or sound of the second subject.

15. The system of claim 14, further comprising:
a third sensor, positioned at a third location and configured to:
  monitor a third sleep parameter relating to the first subject; and
  output a third signal at least partially based on the third sleep parameter;
wherein the control unit is further configured to:
  compare the first signal and the third signal; and
  based at least partially on the comparison, determine whether the first sleep parameter and the third sleep parameter are synchronized.

16. The system of claim 15, wherein:
the first sensor is configured to measure one of a heart rate, a respiration, a movement or sound of the first subject; and
the third sensor is configured to measure a different one of a heart rate, a respiration, a movement or sound of the first subject.

* * * * *